United States Patent [19]

Nemphos et al.

[11] Patent Number: 5,679,862
[45] Date of Patent: Oct. 21, 1997

[54] AMINATION PROCESS

[75] Inventors: Speros Peter Nemphos; Dennis Hearn, both of Pasadena, Tex.

[73] Assignee: Chemical Research & Licensing Company, Pasadena, Tex.

[21] Appl. No.: 621,451

[22] Filed: Mar. 25, 1996

[51] Int. Cl.$^6$ ................................................ C07C 209/16
[52] U.S. Cl. .................... 564/480; 564/474; 564/487; 564/488
[58] Field of Search ........................... 564/480, 474, 564/487, 488

[56] References Cited

U.S. PATENT DOCUMENTS

| | | | |
|---|---|---|---|
| 4,123,462 | 10/1978 | Best | 260/585 |
| 4,404,404 | 9/1983 | Swift et al. | 564/473 |
| 4,683,336 | 7/1987 | Blackhurst | 564/480 |
| 5,175,369 | 12/1992 | Fowlkes | 564/497 |
| 5,352,835 | 10/1994 | Dai et al. | 564/480 |
| 5,431,890 | 7/1995 | Crossland | 422/211 |
| 5,530,127 | 6/1996 | Reif et al. | 544/106 |

OTHER PUBLICATIONS

Kirk–Othmer, *Encylopedia of Chemical Technology*, vol. II p. 276 (1979).
Baiker and Kijenski, *Catalytic Synthesis of Aliphatic Amines* pp. 660–661 and 682–683 (1983).
CA117 (5):47914a CN appln. 1057831A 15 Jan. 1992 Abstract.
CA116(21):213993b DD appln. 296909 A5 19 Dec. 1991 Abstract.

*Primary Examiner*—Brian M. Burn
*Attorney, Agent, or Firm*—Kenneth H. Johnson

[57] ABSTRACT

A process for the amination of aliphatic alkane derivatives such as alcohols (mono and polyhydric) which uses catalytic distillation to take advantage of the condensing distillate within the distillation reaction zone in the distillation column reactor. The operation of the distillation column reactor results in both a liquid and vapor phase within the distillation reaction zone. The catalyst is prepared in the form of a distillation structure. The reaction is carried out in a distillation column reactor at a low hydrogen partial pressure, e.g. in the range of 0.1 psia to less than 10 psia.

16 Claims, 1 Drawing Sheet

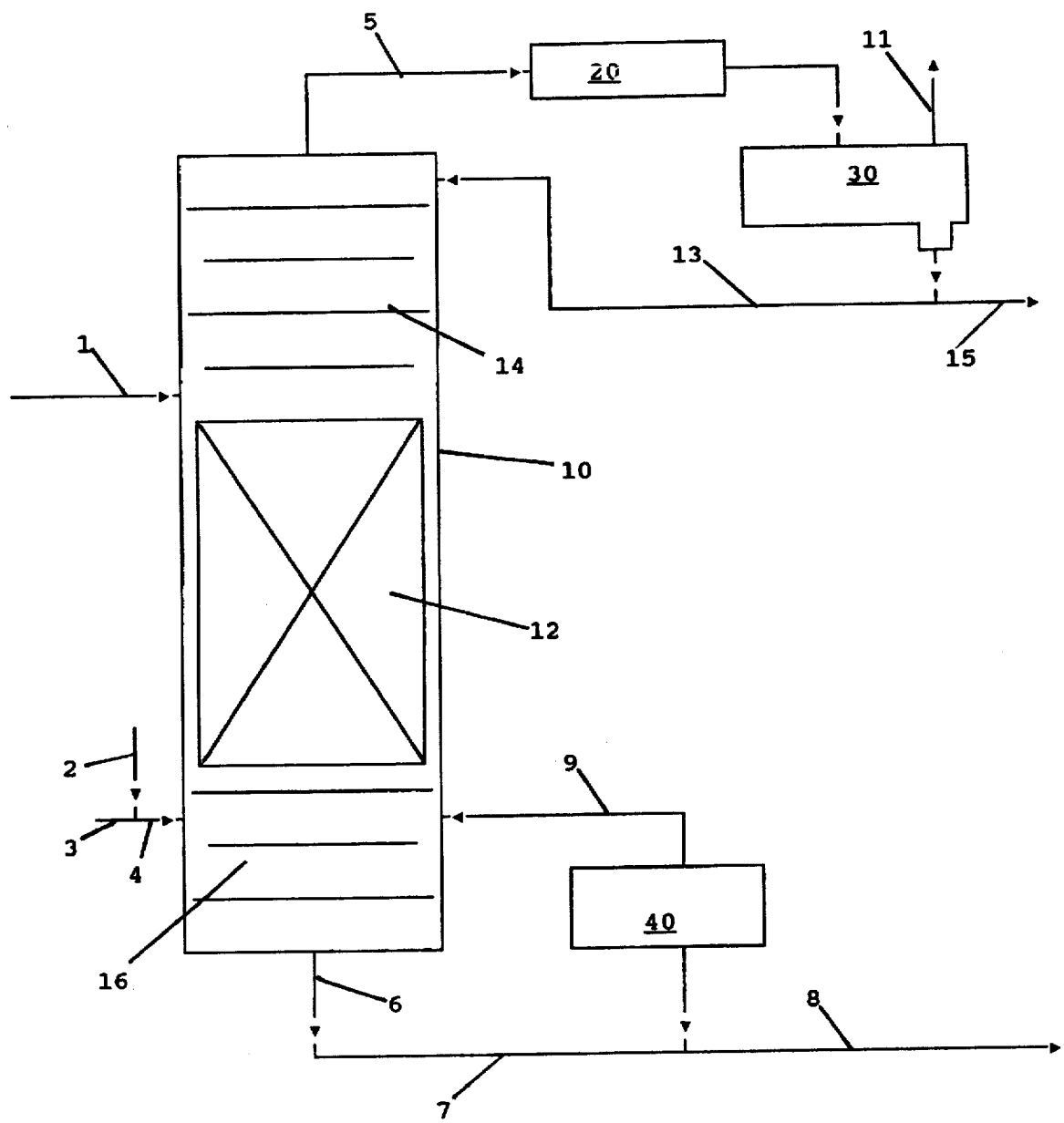

AMINATION PROCESS

BACKGROUND OF THE INVENTION

The present invention particularly concerns the production of lower alkylamines by the catalytic amination of lower aliphatic alkane derivatives such as mono- and polyhydric alcohols, alcoholamines, and compounds from which these alcohols are derived, including epoxides, ketones and alkyleneimines.

The catalytic amination of alcohols is a process which has been long recognized in the prior art. It generally concerns the reaction of alcohol with ammonia in the presence of a hydrogenation catalyst and usually in the presence of hydrogen.

The amine products produced in accordance with the present invention have many uses. In addition to their use as intermediates for synthesizing other chemical materials, they are utilized, for example, in fungicides and insecticides.

U.S. Pat. No. 2,861,995 describes a method of converting ethanolamine to various nitrogen-containing products by using a metal hydrogenation catalyst comprising one or more of nickel, cobalt, copper chromite, catalytic noble metal such as platinum and palladium, and Raney nickel and Raney cobalt. They may be supported on a carrier such as alumina.

U.S. Pat. No. 3,068,290 describes a process for converting ethanolamine to ethylenediamine by using a hydrogenation catalyst, such as described above, in a reaction which is in the liquid phase, under autogenous pressure. The patent also describes a preferred catalyst which is a combination of nickel and magnesium oxides (Ni-MgO), obtained by thermal decomposition of co-precipitated nickel and magnesium formates or oxalates.

U.S. Pat. No. 3,137,730 teaches the conversion of ethylene glycol by using a supported catalyst comprising nickel and copper. U.S. Pat. No. 3,270,059 teaches an amination process in the presence of a supported catalyst which is produced by sintering oxygen compounds of either nickel or cobalt at temperatures in excess of 700° C. and reducing the sintered metal compound by treatment with hydrogen. U.S. Pat. No. 3,766,184 describes a catalyst containing iron with either nickel, cobalt or mixtures thereof. Ruthenium catalysts are also referred to in this and other patents as useful in amination processes.

SUMMARY OF THE INVENTION

The present invention uses catalytic distillation in the amination of aliphatic alkane derivatives to take advantage of the condensing distillate within the distillation reaction zone in the distillation column reactor by concurrently in said distillation column reactor (a) contacting the aliphatic alkane derivatives, hydrogen and ammonia at a hydrogen partial pressure in the range of about 0.1 psia to less than 150 psia, preferably less than 100 psia, e.g., in the range of 0.1 psia to less than 10 psia in the presence of a hydrogenation catalyst prepared in the form of a catalytic distillation structure thereby reacting a portion of the aliphatic alkane derivatives with a portion of the ammonia and hydrogen to form a reaction mixture containing amines, unreacted hydrogen, water and unreacted aliphatic alkane derivatives and fractionally distilling the reaction mixture.

The operation of the distillation column reactor results in both a liquid and vapor phase within the distillation reaction zone. A considerable portion of the vapor is hydrogen and ammonia while a portion is vaporous aliphatic alkane derivatives. Within the distillation reaction zone there is an internal reflux and liquid from an external reflux which cool the rising vapors condensing a portion within the bed.

Without limiting the scope of the invention it is proposed that the mechanism that produces the effectiveness of the present process is the condensation of a portion of the vapors in the reaction system, which occludes sufficient hydrogen in the condensed liquid to obtain the requisite intimate contact between the ammonia, hydrogen and the alcohol in the, presence of the catalyst to result in the production of amines.

BRIEF DESCRIPTION OF THE DRAWING

The FIGURE is a flow diagram in schematic form of one embodiment of the present invention.

DETAILED DESCRIPTION

The alkane derivatives which may be aminated in accordance with the present invention include lower aliphatic alkane derivatives having one or more functional groups. Preferred lower aliphatic alkane derivatives include those containing one to six carbons. The functional groups present may be on the primary, secondary or tertiary carbon atoms. At least one of the functional groups present should be capable of being replaced by an amine group in the catalytic amination process of the present invention. The preferred functional groups include hydroxy, amino, imino groups and combinations of said groups, such as alcohols (mono and polyhydric). Illustrative examples of preferred alkane derivative starting materials include ethanol, ethyleneglycol (ethanediol), monoethanol-amine, ethyleneimine, isopropanol, propanolamines, propanediols, acetone, butanols, butanediols, aminobutanols, pentanols, pentanediols, aminopentanols, hexanols, hexanediols and aminohexanols. The starting materials contemplated herein also include compounds from which the aforementioned may be derived. Preferably, at least one of the functional groups in the starting material is a hydroxy group. Other functional groups which are not replaceable during amination may be present in the alkane starting material in combination or in addition to the replaceable functional groups.

The particular alkane derivative starting materials to be used, of course, depends upon the particular amine product desired to be produced. Generally, the desired aminated product differs from the alkane starting material by the amine group which replaces the non-amine functional group or groups present in the starting material. For example, in the production of ethylene diamine, starting materials include ethylene glycol and monoethanol amine.

The process can thus be considered to comprise:

(a) feeding aliphatic alkane derivatives, hydrogen and ammonia to a distillation column reactor;

(b) contacting the aliphatic alkane derivatives, hydrogen and ammonia at a hydrogen partial pressure in the range of about 0.1 psia to less than 150 psia, preferably less than 100 psia, in the presence of a hydrogenation catalyst prepared in the form of a catalytic distillation structure thereby reacting a portion of the aliphatic alkane derivatives with a portion of the ammonia and hydrogen to form a reaction mixture containing amines, unreacted hydrogen, water and unreacted aliphatic alkane derivatives;

(c) maintaining the pressure in the distillation column reactor such that the reaction mixture is at its boiling point;

(d) removing an overhead from the distillation column reactor comprising vaporous unreacted aliphatic alkane derivatives, water and hydrogen and any lower boiling amines;

(e) condensing substantially all of the aliphatic alkane derivatives removed as overheads from the distillation column reactor;

(f) returning a portion of the condensed aliphatic alkane derivatives (which may include water and lower boiling amines) to the distillation column reactor as reflux; and (g) withdrawing a product from the distillation column.

Since the reaction can result in a mixture of amine products, there may be overheads product, bottoms product and/or side draw products. By adjusting the conditions, one or more products may be favored, for example the amination of ethylene glycol can produce monoethanolamine (MEA), ethylenediamine (EDA) and diethylenediamine (DEDA). At higher ratios of ammonia to alcohol, the production of the lower boiling amines (lower substitution) is favored. In the distillation column reactor, the desired product may also be favored by return of the undesired product to the column. For example returning the monoamine to the column while removing the di and tri amines favors selectivity to the higher substituted amines.

Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

As described the catalytic material employed in the hydrogenation process is in a form to serve as distillation packing. Broadly stated, the catalytic material is a component of a distillation system functioning as both a catalyst and distillation packing, i.e., a packing for a distillation column having both a distillation function and a catalytic function.

The reaction system can be described as heterogenous since the catalyst remains a distinct entity. Any suitable hydrogenation catalyst may be used, for example Group VIII metals of the Periodic Table of Elements as the principal catalytic component, alone or with promoters and modifiers such as palladium/gold, palladium/silver, cobalt/zirconium, nickel and nickel/rhenium preferably deposited on a support such as alumina, fire brick, pumice, carbon, silica, silica-alumina, kieselguhrs, diatomaceous earths silica-titania, resin or the like.

The catalysts may contain various metals in admixture which do not detrimentally affect the catalytic properties of the catalyst. These additional metals, in some amination processes, may actually improve selectivity and activity of the basic catalyst. Certain of these metals may extend the activity life and other physical properties of the catalyst. Examples of catalysts containing additional metal components include Ni-Re-La, Ni-Re-Ca, Ni-Re-Mg, Ni-Re-Sr, Ni-Re-Li, Ni-Re-K, Ni-Re-Ba, Ni-Re-Ce, Ni-Re-W, Ni-Re-Fe, Ni-Re-Ru, Ni-Re-Cu, Ni-Re-Ag, Ni-Re-Zn, Ni-Re-Co, Ni-Re-U, Ni-Re-Ti and Ni-Re-Mn. In order to prepare such catalysts, salts of these additional metals are added in suitable amounts to the impregnation solution containing the nickel and rhenium salts.

A preferred catalyst structure for the present amination comprises at least one plurality of flexible, semi-rigid open mesh tubular elements filed with a particulate catalytic material (catalyst component) and sealed at both ends, intimately associated with and supported by a wire mesh screen coiled into a spiral having a longitudinal axis, said tubular element being arrayed at an angle to the longitudinal axis thereby forming a bale and is described in detail in U.S. Pat. No. 5,431,890 incorporated herein. Such individual elements are similar in appearance to link "sausages".

The flexible, semi-rigid open mesh tubular element filled with a particulate catalytic material preferably has a fastener every 1–12 inches along the length of the tube to form a multiple link shaped catalytic distillation structure. The links formed by the fasteners may be evenly or irregularly spaced.

The bale shaped catalytic distillation structures are formed by placing at least one tubular element on top of the wire mesh screen, such as demister wire, in a diagonal array, such that when the wire mesh screen is rolled up, the rolled structure provides a new and improved catalytic distillation structure. Further embodiments include multiple stack arrangements of alternating wire screen mesh and tubular elements that are rolled into a new bale shaped catalytic distillation structure. The tubular elements on alternating layers are preferably arrayed on the wire mesh screen in opposite directions such that their paths cross. Each tubular element will define a spiral within the bale. Other structures known in the art may be used such as disclosed in U.S. Pat. Nos. 4,443,559 and 5,348,710.

The catalyst component may take several forms. In the case of particulate catalytic material, generally from 60 mm to about 1 mm down through powders, is enclosed in a porous container such as screen wire, or polymeric mesh. The material used to make the container must be inert to the reactants and conditions in the reaction system. The screen wire may be aluminum, steel, stainless steel, and the like. The polymer mesh may be nylon, teflon, glass fibers, i.e., silicate polymer or the like having a softening, e.g., melting temperature higher than 400° F., the temperature of the catalyst bed during the reaction. The mesh or threads per inch of the material used to make the container is such that the catalyst is retained therein and will not pass through the openings in the material. Although the catalyst particles of about 0.15 mm size or powders may be used and particles up to about ¼ inch diameter may be employed in the containers.

The catalyst is activated by a suitable step wherein the impregnated metal is converted into a catalytically active form. This activation may include alloy formation, proper phase orientation of the metals and/or an adjustment in the oxidation level of the metals. An activation step may include a typical reduction process.

In the preferred activation step the atmosphere in contact with the catalyst is hydrogen which is fed over the catalyst at an elevated temperature in the order of 200° to 600° C. for periods of from about 45 minutes to about 4 hours. The specific conditions for reduction are dependent upon the particular catalyst composition being activated.

Prior to the activation step, the catalyst may be optionally calcined. The catalyst is heated to temperatures in the range of about 300° to 500° C. for 45 minutes to about 3 hours or more. It is preferred that the calcining be carried out in air.

As indicated above, the amination of alkane derivatives is a process which has been extensively investigated and is well documented in the prior art. The reaction conditions for the process to occur are generally known but are particularly dependent upon the activity of the amination catalyst present.

The amination of alcohols involves a reaction between ammonia and alcohol in the presence of hydrogen gas. The catalytic amination process consists of hydrogenation and dehydrogenation reactions. The mechanism of these various reactions have been extensively discussed in the literature as illustrated in the seven reaction equations below as series of sequential steps:

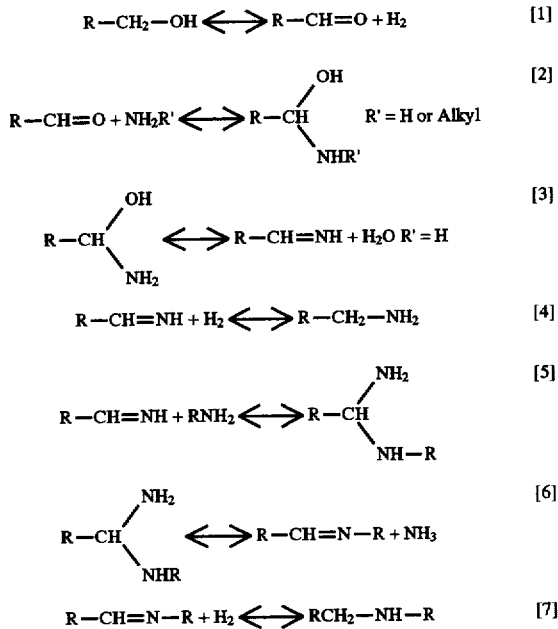

The first step in the amination process is a reversible dehydrogenation of the alcohol to give an intermediate carbonyl [1]. The aldehyde is then converted to an aminoalcohol [2] by reaction with ammonia or an amine present in the reaction mixture. The aminoalcohol then loses water to form the imine [3]. The imine is then hydrogenated to the amine [4]. Formulas 5, 6, and 7 illustrate the possible products formed by a reaction of the intermediate imine with ammonia or amines present in the reaction mixture.

As the equations show all of the proposed reaction steps are reversible. The operation of reactive or catalytic distillation lies in an understanding of the principles associated with distillation. First, because the reaction is occurring concurrently with distillation, the initial reaction product is removed from the reaction zone as quickly as it is formed. The removal of the product(s) minimizes polysubstitution, decomposition of the product(s) and/or polymer. Second, because the organic aromatic compound is boiling, the temperature of the reaction is controlled by the boiling point of that component at the system pressure. The heat of the reaction simply creates more boil up, but no increase in temperature. Third, the reaction has an increased driving force because the reaction products have been removed and cannot contribute to a reverse reaction (Le Chatelier's Principle).

The present invention carries out the method in a catalyst packed column which can be appreciated to contain a vapor phase and some liquid phase as in any distillation. The distillation column reactor is operated at a pressure such that the reaction mixture is boiling in the bed of catalyst.

The present process operates at overhead pressure of said distillation column reactor in the range between 0 and 300 psig, preferably 200 or most suitable 35 to 120 psig and temperatures in said distillation reaction bottoms zone in the range of 150° to 500° F., preferably 250° to 450° F., e.g. 300° to 400° F. at the requisite hydrogen partial pressures. The feed weight hourly space velocity (WHSV), which is herein understood to mean the unit weight of feed per hour entering the reaction distillation column per unit weight of catalyst in the catalytic distillation structures, may vary over a very wide range within the other condition perimeters, e.g. 0.1 to 35.

In the current process the temperature is controlled by operating the reactor at a given pressure to allow partial vaporization of the reaction mixture. The exothermic heat of reaction is thus dissipated by the latent heat of vaporization of the mixture. The vaporized portion is taken as overheads and a portion of the condensible material condensed and returned to the column as reflux.

The downward flowing liquid causes additional condensation within the reactor as is normal in any distillation. The contact of the condensing liquid within the column provides excellent mass transfer for dissolving the hydrogen and ammonia within the reaction liquid and concurrent transfer of the reaction mixture to the catalytic sites. It is thought that this condensing mode of operation results in the excellent conversion and selectivity of the instant process and allows the lower hydrogen partial pressures and reactor temperatures noted. A further benefit that this reaction may gain from catalytic distillation is the washing effect that the internal reflux provides to the catalyst thereby reducing polymer build up and coking. Internal reflux may vary over the range of 0.2 to 20 L/D (wt. liquid just below the catalyst bed/wt. distillate) and give excellent results.

Hydrogen must be supplied in at least stoichiometric quantities. The molar ratio of ammonia to aliphatic alkane derivative is preferably at least 1:1. Hydrogen should be present in the molar ratio of about 4:1 of hydrogen to ammonia. The amount of hydrogen gas present in the amination process of the present invention is not critical. Usually, hydrogen is added in an amount sufficient to maintain the catalyst in an active state. A preferred amination process is carried out where the hydrogen is present in an amount wherein the hydrogen to ammonia mole ratio is greater than 1 and preferably less than the ratio 1000:1.

In the amination process of the present invention, the alkane derivative starting material is reacted at an elevated temperature with ammonia in the presence of hydrogen and the catalyst. The temperature for the reaction depends upon the particular starting material, ratios of reactants, and most importantly, the activity of the catalyst used.

The ammonia employed in the reaction may be anhydrous or may contain small amounts of water. Any water introduced into the reaction mixture with the ammonia should be considered when conversion of the reaction is evaluated by the presence of water in the final mixture.

Normally, the process is run in an excess of ammonia to ensure reactions with ammonia and not an amine present in the reaction mixture. This is one means of improving the yield of the desired aliphatic alkylamine product. A excess of ammonia may be present.

In the amination processes of the present invention, the ammonia should be present in an amount at least equivalent to the stoichiometric amount required by the alkane derivative reactant. The ammonia should preferably be present in an amount between 2 times and 30 times the stoichiometric amount required.

Referring now to the FIGURE there is shown a flow diagram of one embodiment of the invention. N-butanol is fed via line 1 to the distillation column reactor 10 at a point above the catalyst bed 12 containing the catalytic distillation structure. Hydrogen is fed via flow line 2 and ammonia via flow line 3 which are combined in flow line 4 and fed below the bed 12. Overheads containing the cyclohexyl amine and unreacted n-butanol, monobutyl amine, ammonia and hydrogen are taken via flow line 5 and passed through partial condenser 20 wherein the condensible materials are condensed. The overheads are then collected in receiver/separator 30 wherein the hydrogen and other uncondensed vapors, e.g., ammonia, are separated and removed via flow line 11 for recycle (not shown) if desired to the hydrogen feed or at a point below the catalyst bed. Product monobutyl amine stream is taken via flow line 15 (for further separation of amine from water and butanol (not shown) and a portion of the condensed overheads is returned to the distillation column reactor 10 as reflux via flow line 13.

Bottoms are taken via flow line 6 and a portion are passed through reboiler 40 to balance heat for the column 10. The bottoms contain tributyl amine. A portion of the bottoms may be recycled via flow line 9 for conversion to monobutyl amine. The amount of recycled bottoms will depend on the desired product(s). If the tributyl amine is the desired product only so much of the reboiler bottoms are returned to the column as necessary to maintain the reaction conditions and the balance is removed via line 8. If the mono- or di- amines are the target products, then a bottoms draw via flow line 8 is provided to prevent build up of the heavies, with the major portion of the reboiler bottoms being returned to the distillation column reactor via line 9.

The distillation column reactor is provided with rectifying section 14 to separate unreacted n-butanol from the product and stripping section 16 to insure that no butanol or mono- or di- amine product is removed as bottoms. In this reaction azeotropes are formed between the water by-product and n-butanol feed and the amine products as described in the TABLE I.

TABLE I

| COMPONENT | B.P. (°C.) | AZEOTROPE B.P. (°C.) | AZEOTROPE COMPOSITION (MOLE %) |
|---|---|---|---|
| a) n-butyl amine | 77 | 75 | 98 |
| water | 100 | | 2 |
| b) di n-butyl amine | 160 | 97 | 50 |
| water | 100 | | 50 |
| c) tri n-butyl amine | 214 | 100 | 18 |
| water | 100 | | 82 |
| d) n-butyl alcohol | 118 | 92 | 58 |
| water | 100 | | 42 |

In the following examples a twenty five foot tall one inch diameter distillation column reactor was used. The catalyst used was Calsicat E-475 SR, 56% nickel on alumina in the form of 3/16" spheres. The catalyst was packaged as six inch long by 0.75 inch diameter "sausages" as described above wrapped with 100 mesh stainless steel screen.

EXAMPLE 1

In this example 0.7 pound of the 3/16" Calsicat E-475 SR (55% Ni on alumia) prepared as described above was loaded into the middle 10 feet of the distillation column reactor. The top and bottom 7.5 feet were packed with ceramic saddles. Typical amination conditions and results for this run are shown in TABLE II.

TABLE II

| FEED RATE (lbs/hr) | | |
|---|---|---|
| n-Butanol | 1 | 2 |
| NH₃ | 0.4 | 1.2 |
| OVERHEAD PRESSURE (psig) | 100 | 70 |
| OVERHEAD FEED RATE (lbs/hr) | 0.9 | 2 |

TABLE II-continued

| BOTTOMS FEED RATE (lbs/hr) | 0.15 | <0.1 |
|---|---|---|
| CATALYST BED TEMP. (°F.) | 280 | 290 |
| PRODUCTIVITY (lbs/hr/lbs cat) Monoamine | 0.24 | 0.28 |
| CONVERSION (%) n-Butanol to Monoamine | 17 | 10 |

The test was run for 700 hours resulting in several major conclusions. Total production of amines was favored at higher column pressure i.e., 100 psig (first 300 run hours) and also when the alcohol was fed at the top of the catalyst bed vs at the bottom. Ammonia and hydrogen were fed at the bottom of the tower.

Shifting of productivity in favor of one amine over the other is possible via adjusting process conditions in the column and feed ratios as discussed below.

Monobutyl Amine Production:

Mono n-butyl amine (BP 77° C.) is distilled off the top of the column as it is the lowest boiling product. It was collected together with the water by-product of the amination reaction and the unreacted n-butanol which is distilled as an azeotrope with the water (58/42 ratio, BP 92° C.). Monobutyl amine productivity is maximized according to the literature by feeding a high ratio of NH₃/n-butanol to the reactor, e.g. in the range of 3 to 6. In this run ratios were limited to 1 to 3. It was also found that faster throughput rates of alcohol through the catalyst bed, i.e. higher takeoff rates at the top of the tower yield higher productivity and selectivity of the monobutyl amine product. Typical overhead distillate compositions in this run during periods of maximum monobutyl amine production were 15–25% monobutyl amine, 10–15% water and 50–70% n-butyl alcohol. Other reaction conditions that favored increased productivity of the monobutyl amine were higher pressure ≧100 psig. When monobutyl amine is the desired product most of the feed stream is taken off the top of the column as the distillate, with only a small purge (5–20%) taken off as bottoms draw to avoid buildup of high boiling impurities in the reboiler.

Tri n-butyl Amine:

This is the highest boiling of the butyl amines (BP 214° C.) and it always concentrates at the bottom of the column. Controlling the reboiler temperature at 600° F., 90–96% pure tri n-butyl amine was taken from the column as the bottom draw at a productivity rate of 0.2 to 0.3 lb/lb catalyst.

If desired as a product, running the column with a lower ammonia/n butanol feed ratio will increase the tributyl amine productivity further. If not desired as a product, reducing the reboiler temperature, and feeding ammonia through the reboiler would shift the equilibrium toward monobutyl and dibutyl amine production.

Di n-butyl Amine:

This intermediate boiling amine by-product tends to stay at the bottom of the column. If desired as a product, it was shown in the run that by maintaining the reboiler temperature at an intermediate range of ~500° F., 80–90% purity dibutyl amine can be produced as the bottom draw at productivity rates of 0.2–0.3 lbs/lb catalyst.

The three amine products discussed above represent >95% yield of the converted n-butanol. Impurities of significance identified were about 1–2% of "heavier" (higher boiling amines than tributyl amine) in the bottom stream and 0.1–0.2% dibutyl amine in the overhead distillate.

Catalyst Life:

No significant reduction in productivity was noted over the 700 hour run length of this experiment. It should be noted that hydrogen gas was passed continuously through the column throughout the run. Its main function is believed to inhibit deposits of high molecular weight byproducts on the catalyst causing deactivation. It is assumed that (a) the H₂ flowing through the catalyst bed and (b) the washing action of the refluxing stream over the catalyst tend to maintain the catalyst clean and prolong its activity.

EXAMPLE 2

The same apparatus and feeds used in Example 1 were employed in this run. The main objective in this run was to demonstrate the ability to maximize productivity of tributyl amine and minimize the monobutyl. This was achieved by:
a) maintaining high temperature in the reboiler (>600° F.) and in the catalyst bed (<300° F.), and
b) maintaining the molar ratio of ammonia/butanol at ≦2.

These conditions allow all the by-product water plus the unreacted butanol to be taken off the top of the column with little monobutyl amine (1–9%). The bottom draw on the other hand contains no water or monobutyl product and is essentially >95% tributyl amine.

It appears, also, that dibutyl amine at high selectivity can be drawn off the bottom of the tower by adjusting the temperature conditions lower, and/or increasing the NH₃/alcohol feed ratio. As an alternate approach dibutyl amine product which maximizes at the lower part of the catalyst bed and could be taken of as a side draw there. If not a desired product it reaches equilibrium as it converts to tributyl amine and it can be left in the tower to maximize the tributyl amine product. Typical amination conditions and result for this run are shown in TABLE III.

TABLE III

| FEED RATE (lbs/hr) | | |
| --- | --- | --- |
| n-Butanol | 0.5 | 0.6 |
| NH₃ | 0.15 | 0.2 |
| OVERHEAD PRESSURE (psig) | 150 | 150 |
| OVERHEAD FEED RATE (lbs/hr) | 0.2 | 0.3 |
| BOTTOMS FEED RATE (lbs/hr) | 0.3 | 0.35 |
| CATALYST BED TEMP. (°F.) | 300 | 310 |
| PRODUCTIVITY (lbs/hr/lbs cat) Tributylamine | 0.26 | 0.38 |
| CONVERSION (%) n-Butanol to Tributylamine | 43.6 | 53.2 |

EXAMPLE 3

Using the distillation column and feeds of Example 1 at conditions 20–30 psig and 500°–550° F. reboiler temperature it was possible to purify the tributyl amine product up to 95% purity. The bottom stream product of this amination reaction is essentially >90% tributyl amine depending on process conditions. It was concluded the high reboiler temperature caused decomposition of the amines.

The invention claimed is:

1. A process for the amination of aliphatic alkane derivatives in a distillation column reactor by concurrently in said distillation column reactor (a) contacting aliphatic alkane derivatives having one or more functional groups, hydrogen and ammonia at a hydrogen partial pressure in the range of about 0.1 psia to less than 150 psia in the presence of a hydrogenation catalyst prepared in the form of a catalytic distillation structure thereby reacting a portion of the aliphatic alkane derivatives with a portion of the ammonia and hydrogen to form a reaction mixture containing amines, unreacted hydrogen, water and unreacted aliphatic alkane derivatives and (b) fractionally distilling the reaction mixture.

2. An amination process comprising:

(a) feeding aliphatic alkane derivatives, hydrogen and ammonia to a distillation column reactor;

(b) contacting the aliphatic alkane derivatives having one or more functional groups, hydrogen and ammonia at a hydrogen partial pressure in the range of about 0.1 psia to less than 150 psia in the presence of a hydrogenation catalyst prepared in the form of a catalytic distillation structure thereby reacting a portion of the aliphatic alkane derivatives with a portion of the ammonia and hydrogen to form a reaction mixture containing amines, unreacted hydrogen, water and unreacted aliphatic alkane derivatives;

(c) maintaining the pressure in the distillation column reactor such that the reaction mixture is at its boiling point;

(d) removing an overhead from the distillation column reactor comprising vaporous unreacted aliphatic alkane derivatives, water and hydrogen and any lower boiling amines;

(e) condensing substantially all of the aliphatic alkane derivatives removed as overheads from the distillation column reactor;

(f) returning a portion of the condensed aliphatic alkane derivatives (which may include water and lower boiling amines) to the distillation column reactor as reflux; and (g) withdrawing a product from the distillation column.

3. The process according to claim 2 wherein the aliphatic alkane derivatives contain one to six carbons.

4. The process according to claim 2 wherein the aliphatic alkane derivatives have at least one of the functional group capable of being replaced by an amine group.

5. The process according to claim 4 wherein the functional groups present may be on the primary, secondary or tertiary carbon atoms.

6. The process according to claim 2 wherein the functional groups are selected from the group consisting of hydroxy, amino, imino and combinations thereof.

7. The process according to claim 2 wherein the aliphatic alkane derivatives comprise an alcohol.

8. The process according to claim 7 wherein the alcohol comprises n-butanol.

9. The process according to claim 2 wherein the catalyst comprises a supported Group VIII metal or metal compound.

10. The process according to claim 2 wherein the catalyst comprises a Ni supported on alumina.

11. The process according to claim 2 wherein the total pressure is in the range of 0 to 300 psig.

12. The process according to claim 11 wherein the total pressure is less than 200 psig.

13. The process according to claim 2 wherein the hydrogen partial pressure is less than 100 psia.

14. The process according to claim 2 wherein the temperature is in the range of 150° to 500° F.

15. The process according to claim 14 wherein the temperature is in the range of 250° to 450° F.

16. The process according to claim 13 wherein the hydrogen partial pressure is in the range of 0.1 pisa to less than 10 pisa.

* * * * *